US00PP10371P

United States Patent [19]

Ebihara

[11] Patent Number: Plant 10,371

[45] Date of Patent: May 5, 1998

[54] HYDRANGEA PLANT NAMED 'FRAU NOBUKO'

[75] Inventor: Hiroshi Ebihara, Ninomiya-machi, Japan

[73] Assignee: Miyoshi & Co. Ltd., Tokyo, Japan

[21] Appl. No.: 731,694

[22] Filed: Oct. 17, 1996

[51] Int. Cl.[6] ..... A01H 5/00

[52] U.S. Cl. ..... Plt./67.1

[58] Field of Search ..... Plt./67.1

[56] References Cited

U.S. PATENT DOCUMENTS

| | | | |
|---|---|---|---|
| P.P. 9,499 | 4/1996 | Ebihara | Plt./67.1 |
| P.P. 9,500 | 4/1996 | Ebihara | Plt./67.1 |
| P.P. 9,510 | 4/1996 | Ebihara | Plt./67.1 |

OTHER PUBLICATIONS

UPOVROM Disk 1997/03 Result Sheet ① GTITM UPOVROM Listing NZ PBR SHM 089 published Jul. 14, 1996.

UPOVROM Disk 1997/03 Result Sheet ② GTITM UPOVROM Listing NL PBR HDG 0016 published Jul. 16, 1994.

UPOVROM Disk 1997/03 Result Sheet ③ GTITM UPOVROM Listing AU PBR 96115 filing date May 31, 1996.

*Primary Examiner*—James R. Feyrer
*Assistant Examiner*—Kent L. Bell
*Attorney, Agent, or Firm*—James R. Cypher

[57] ABSTRACT

This invention relates to a new and distinct cultivar of *Hydrangea macrophylla* (Thunb.) named 'Frau Nobuko' which originated as a seedling from the inventor's controlled hybridization of the *Hydrangea macrophylla* cultivars 'Madam Blumkock' and 'Silver Edge' and is distinguished from its parents by the combination of the attractive pigmentation pattern of its sepals which is predominantly colored with narrow, irregular, white edges; its moderately ruffled edges with occasionally serrations; and its dense inflorescence on a strong stem that does not require staking for support. Sepal pigmentation of individual *Hydrangea macrophylla* plants depends on the nutrients and pH of the growing medium. The sepals of 'Madam Blumkock' are uniformly pink and the sepals of 'Silver Edge' are uniformly red with a white edge. The new variety 'Frau Nobuko' further possesses the favorable characteristics of a compact growth habit, long lasting large flowers an a strong peduncle, and ability to be easily forced in a greenhouse for flowering in the spring.

1 Drawing Sheet

BACKGROUND OF THE INVENTION

This invention relates to a new and distinct cultivar of the Saxifragaceae family. The botanical name of the plant is *Hydrangea macrophylla* (Thunb.). The varietal denomination is 'Frau Nobuko'. The new cultivar originated as a seedling from the inventor's controlled crossing as pollen and seed parents, respectively, the varieties known as 'Madam Blumkock' and 'Silver Edge' in Tochigi-Prefecture, Japan. 'Frau Nobuko' was discovered and selected as one flowering plant within the progeny of the stated parentage in a controlled environment.

'Frau Nobuko' is distinguished from its parents and all other varieties of *Hydrangea macrophylia* of which I am aware, by the combination of the attractive pigmentation pattern of its sepals which is predominantly colored with narrow, irregular, white edges; its moderately ruffled edges with occasionally serrations; and its dense inflorescence on a strong stem that does not require staking for support. This new cultivar has been successfully asexually reproduced by vegetative cuttings under controlled environmental conditions at a commercial nursery in Tochigi-Prefecture, Japan, under the direction of the inventor over a ten year period from 1986 to 1996, with its distinguishing characteristics remaining stable. Sepal pigmentation of individual *Hydrangea macrophylla* plants depends on the nutrients and pH of the growing medium. Sepal color of 'Frau Nobuko' is predominantly blue or red with a narrow, irregular white edge pattern. The pigmentation is darkest at the apex and fades slightly as it progresses across the length and width of the sepals, and then turns white as far as 5 mm from the edge.

The sepal coloration of the seed parent 'Silver Edge' is uniformly red with a white edge. The sepals of the pollen parent 'Madam Blumkock' are uniformly pink.

The new variety of Hydrangea as described herein is further characterized by its compact growth habit, the ease with which it can be forced in a greenhouse, and its large, long lasting flowers which do not need to be staked, making it desirable for pot culture.

DESCRIPTION OF THE DRAWINGS

The accompanying drawings consist of color photographs that show the typical plant form, including the inflorescence, foliage, and unique sepal pigmentation pattern. 'Frau Nobuko' is shown with a pink and white sepal pigmentation pattern, but a blue and white pigmentation pattern is also possible by manipulation of the nutrient amendments and the pH of the growing medium. The colors are represented as truly as possible using conventional photographic procedures.

DESCRIPTION OF THE NEW PLANT

Figure 1:
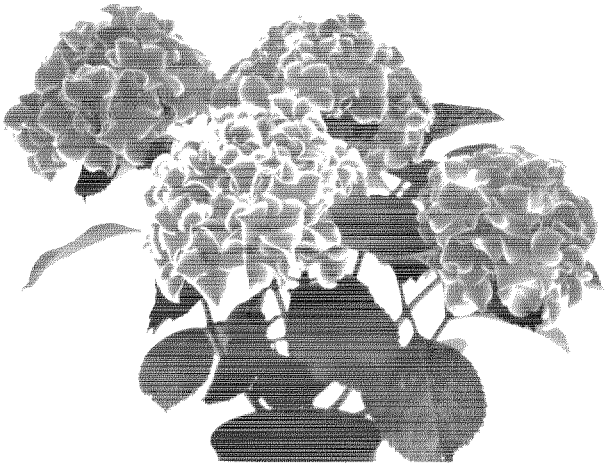
FIG. 1 is a view of the entire plant showing its form, compact growth habit, dark green foliage, dense and large inflorescence, and unique sepal pigmentation pattern.
Figure 2:
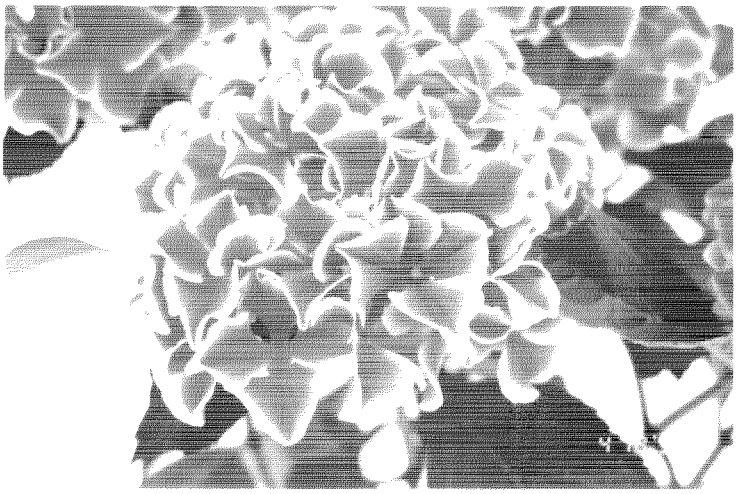
FIG. 2 is a close-up view of a flower head illustrating the unique color pigmentation pattern, reniform sepal shape, and ruffled, serrated edges.

'Frau Nobuko' has not been observed under all possible environmental conditions. The phenotype may vary significantly with variations in environment such as temperature, light intensity and day-length. The following is a detailed description of the new cultivar as forced under the prevailing day-lengths at Half Moon Bay, Calif. under commercial greenhouse conditions at a time appropriate for the sale of the cultivar in the spring. The color determinations were made with The Royal Horticultural Society (R.H.S.) Colour Chart.

The Plant

Origin: Seedling.

Parentage:

*Seed parent.*—*Hydrangea macrophylla* (Thunb) 'Silver Edge'.

*Pollen parent.*—*Hydrangea macrophylla* (Thunb) 'Madam Blumkock'.

Classification:

*Botanic.*—*Hydrangea macrophylla* (Thunb.) 'Frau Nobuko'.

*Commercial.*—Florist Hydrangea 'Frau Nobuko'.

Form: Upright, compact shrub.

Height: Flowering shoots reach 30 cm. in a 4" pot.

Growth: Upright, vigorous growth habit; when forced to bloom in greenhouse the addition of growth regulators is necessary to control height.

Flowerhead: Terminal; composite, rounded clusters of small florets; dome-shaped and dense; composed of florets carried on sturdy peduncles.

Stems: Colorless lenticels; lateral buds are reddish; reddish coloration above and below leaf attachment sites.

Foliage: Abundant.

*Size of leaf.*—As large as 72 mm wide by 105 mm long.

*Shape of leaf.*—Elliptic with acute base and apex; margins are serrate.

*Texture.*—Glabrous; veins dominate on the underside of the leaf and are sunken on the leaf surface.

*Color.*—Upper side is R.H.S. 137 A (green group); under side is R.H.S. 137 C (green group); veins are R.H.S. 145 C (yellow-green group).

*Petioles.*—24 mm long.

The Bud

Form: Globose; with 4 to 5 connate petals. Buds in the very center of the inflorescence are non-sepalous. The majority of buds have sepals.

Size: 3 mm.

Aspect: Smooth.

Rate of opening: Buds with sepals opening more slowly than buds without sepals.

Color: Mature stage is R.H.S. 83D violet group.

Arrangement: Borne on 5 branched panicles.

Inflorescence

Time of blooming: Forced in approximately 80 days at 19° C. night temperatures.

Form: Paniculate. Both sterile, sepalous florets and fertile, non-sepalous florets borne on same panicle.

Size of inflorescence: Individual inflorescence size is dependent on the number of inflorescences per plant. The large inflorescences have been measured with a 15.24 cm diameter, and a 43.18 cm. circumference on a 4 bloom plant. Usually 15.24 cm diameter on a 3+ bloom plant.

Shape: Spherical clusters of small florets; sepalous florets are ruffled and overlap one another. Sepals are persistent. Sepals elongate and mature as the inflorescence matures. Non-sepalous, are inconspicuous and hidden by sepalous florets. The inflorescence is dense.

Appearance: Showy.

Persistence: 4 or more weeks.

Fragrance: Faintly sweet.

Fruit: None.

Reproductive organs:

*Stamens.*—8 present. Pollen is white.

*Stigma.*—2 pronged stigma.

Sepalous florets:

*Number of sepals.*—3 to 5 sepals per floret, usually 4.

*Aspect of sepals.*—Smooth.

*Shape of sepals.*—Reniform with acuminate apex; moderately ruffled, edges are occasionally serrate.

*Size of sepals.*—Sepals of almost equal size; not much difference in size in a four sepal floret (less than 1 cm. difference); slightly more difference in a 5 sepaled floret.

*Size of one large 4 petaled floret.*—50 mm. wide by 51 mm. long.

*Coloration of sepals.*—Sepal color varies according to the soil pH and nutritional amendments supplied. Predominately pink or blue with a narrow, irregular white edge; amount of white edge varies depending on the age of the flower and sepal location within the flower; aged sepals are almost entirely pink or blue; mature sepals have approximately a white edge of 5 mm. Pink Flower: R.H.S. red purple group 64B. Edge: R.H.S. white group 155C.

I claim:

1. A new and distinct hybrid plant variety of the Saxifragaceae family substantially as herein shown and described.

* * * * *